USOO5792961A

United States Patent [19]
Giebner et al.

[11] Patent Number: 5,792,961
[45] Date of Patent: Aug. 11, 1998

[54] PORTABLE MOTORIZED FASTENER TESTER

[75] Inventors: Thomas P. Giebner, Gulfport; Christopher S. Giebner, Treasure Island; Donald K. Matthews, Holiday, all of Fla.

[73] Assignee: Giebner Enterprises, Inc., St. Petersburg, Fla.

[21] Appl. No.: 835,921

[22] Filed: Apr. 10, 1997

[51] Int. Cl.$^6$ ..................................................... G01N 3/02
[52] U.S. Cl. ........................... 73/826; 73/835; 73/786
[58] Field of Search ........................... 73/826, 827, 834, 73/786, 862.38, 835

[56] References Cited

U.S. PATENT DOCUMENTS

| 3,563,087 | 2/1971 | Brunnelle et al. | 73/95 |
| 3,792,608 | 2/1974 | Holm et al. | 73/97 |
| 3,942,368 | 3/1976 | Hoyt | 73/141 |
| 4,217,776 | 8/1980 | McCall | 73/862.53 |
| 4,554,838 | 11/1985 | Paus | 73/834 |
| 4,662,227 | 5/1987 | Peterson | 73/834 |
| 4,753,115 | 6/1988 | Moody | 73/862.1 |

FOREIGN PATENT DOCUMENTS

| 2747329 | 4/1979 | Germany | 73/862 |
| 405087715 | 4/1993 | Japan | 73/826 |

OTHER PUBLICATIONS

Battery Operated Motorized Digital Fastener Testers, Comten Industries, Jan. 1, 1996.
Series 301W Fastener Testers, Comten Industries no date.
Heeley-Brown Company, Pull-Out Tester no date.

Primary Examiner—George M. Dombroske
Assistant Examiner—Max H. Noori
Attorney, Agent, or Firm—Stein, Schifino & Van Der Wall

[57] ABSTRACT

A portable fastener tester system for measuring the pullout strength of a fastener that is comprised of an electronic processing unit electrically coupled to a load cell, an optical reader, an opto chopper disc, and a display, a motor having a shaft coupled to a small drive gear which engages a large drive gear, and a tester assembly comprised of a driving member, a case housing, a power nut assembly and a captured nut retained within the power nut assembly. The captured nut is forceably rotated by the motor and engaged small and large drive gears so to foreceably translate the driving member upward through the power nut assembly thereby applying a pulling force on a fastener being tested. The load cell being utilized to transfer the pulling force from the driving member to the fastener, electrically sense the applied force and transmit data to the electronic processing unit for being displayed to the user. The portable fastener tester system providing for a constant rate of travel of the driving member and fastener during testing thereby providing for highly accurate, precise and repeatable measurement results.

21 Claims, 9 Drawing Sheets

PORTABLE MOTORIZED FASTENER TESTER

BACKGROUND OF THE INVENTION

1. Field of the Invention

This invention relates to a fastener tester and, more particularly, a portable motorized fastener tester having a motorized drive capability and a digital readout display for use in testing the pullout strength of fasteners secured to a structure, such as fasteners on a roof for securing shingles.

2. Description of the Background Art

In building construction, it is common practice in the industry to utilize fasteners for securing down material to a structure. In particular, it is standard in the industry to use fasteners to secure shingles and other materials to a roof surface. In doing such, there are standard codes that must be met regarding the holding strength of the fasteners, as may be affected by high winds, rain and other inclement weather. In assuring that the fasteners are being applied properly to provide an adequate holding strength within the standard code guidelines established by the construction industry, it is a requirement that a sampling of the fasteners be regularly tested for pullout strength. In accomplishing such testing, various types of fastener testers have been utilized with only tolerable accuracy and poor repeatability.

Presently, there exists many different types of fastener testers on the market today. However, none of the currently available portable fastener testers provide for a constant rate of travel (CRT) of the fastener during test as well as are automatic and computer driven so to provide the precise measurement accuracies that are required today in the building/construction industry. Presently, all the portable fastener testers that exist today are manually operated and, hence, provide measurement accuracies that are limited by the operator's physical ability to manually operate and gradually apply the pulling force to the fastener being tested. Hence, the operator can manipulate the results by increasing or decreasing the rate of travel of the fastener during test. This limitation causes repeatability problems as well as significantly reduces the measurement accuracies in that tolerances can not be rigidly adhered to by the operator.

Some representative fastener testers are disclosed in U.S. Pat. Nos. 3,563,087, 3,797,608, 3,942,368, 4,662,227, and 4,753,115, the disclosures of which are hereby incorporated by reference herein. While the above listed fastener testers all provide for the manual testing of fasteners for pullout strength characteristics, many disadvantages exist and are associated with their use in that accuracy and repeatability is compromised. All of the listed testers are manual and lack the ability to produce precise measurements and deliver a controlled rate of travel of the fastener during test.

Therefore, it is an object of this invention to provide an improvement which overcomes the aforementioned inadequacies of the prior art devices and provides an improvement which is a significant contribution to the advancement of the fastener pullout strength testing art.

Another object of this invention is to provide a portable fastener tester system that facilitates the obtaining of measurements that are repeatable and reliable.

Another object of this invention is to provide a portable fastener tester system that is highly accurate and facilitates the determining of precise measurements.

Another object of this invention is to provide a portable fastener tester system that is an automated system which removes the disadvantages associated with operator error and operator inconsistencies by utilizing an electronic processing unit to control the system.

Another object of this invention is to provide a portable fastener tester system that utilizes a load cell for sensing and transmitting precise measurements of the pulling force applied to the fastener being tested.

Another object of this invention is to provide a fastener tester system that operates at a selectable constant rate of speed in order to produce repeatable results and pinpoint the precise minimum amount of force required to dislodge the fastener.

Another object of this invention is to provide a portable fastener tester system that is simple to set up and easy to operate.

Another object of this invention is to provide a portable fastener tester system in the form of an automated system that is readily portable and self contained having its own power source.

Another object of this invention is to provide a portable fastener tester system for testing the pullout strength of a fastener secured to a structure, the portable fastener tester system comprising in combination: a tester assembly capable of being positioned on a structure to facilitate testing of the fastener, the tester assembly including a driving member capable of being coupled relative to the fastener; control means for controlling the operation of the tester assembly and indicating measurement results, the control means being coupled to the tester assembly; and driving means for applying force upon the driving member, the driving means being coupled relative to the driving member of the tester assembly, whereby the tester assembly is positioned on the structure in coupled relation to the fastener to be tested and the control means initiates operation of the tester assembly and controls the driving means so as to act upon the driving member and apply force upon the fastener so to result in translation of the fastener at a constant rate of speed wherein the precise pullout strength of the fastener is determined and indicated.

The foregoing has outlined some of the pertinent objects of the invention. These objects should be construed to be merely illustrative of some of the more prominent features and applications of the intended invention. Many other beneficial results can be obtained by applying the disclosed invention in a different manner or by modifying the invention within the scope of the disclosure. Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention comprises a portable fastener tester system that is automated and electronically controlled so to provide for the removal of the fastener at a constant rate of travel during test to facilitate obtaining highly accurate, precise and repeatable measurement results. The portable fastener tester system of the present invention is comprised generally of a tester assembly, a driving means and a control means. The tester assembly includes a driving member that is threadedly engaged relative to the driving means and utilized to apply force to a fastener when the portable fastener tester system is being operated. The control means is comprised of various electronic components assembled for controlling the driving means engaged relative to the driving member, and determining the pullout strength. The tester assembly is primarily comprised of the driving member which is threadingly received by a captured nut which is retained within a power nut assembly such that when the driving means is applying force to the captured nut, the driving member is drawn upward thereby producing a pulling force on the fastener being tested. The captured nut, being retained within the power nut assembly, is forced to rotate while being retained in a constant vertical position by the power nut assembly, thereby causing the driving member to threadingly translate therethrough.

Coupled at one end of the driving member is a load cell which detects the force being applied to the fastener. The load cell transmits the measured applied force to the microprocessor within the control means wherein the pullout strength is calculated and displayed to the user.

The driving means is generally comprised of an electrical motor which is mounted within the tester assembly and provides the uniform and constant rate of travel of the driving member and fastener coupled relative thereto. The speed of the motor is controlled by the control means by way of an opto chopper disc which is constantly scanned by an optical reader that tracks and reports the actual speed of the motor to the microprocessor wherein adjustments are made accordingly to ensure a constant speed and, thus, a constant rate of travel of the fastener during withdrawal in a test. The maintained constant speed is at a rate that is selectable when initiating the test.

Before conducting a test on a fastener installed in a structure, the portable fastener tester system is preliminarily prepared via the control means and set up in a testing configuration relative to an installed fastener. Once mounted on a structure in a coupled relationship to a fastener, the test is run automatically by the control means.

An important feature of the present invention is that the portable fastener tester system facilitates the obtaining of highly accurate and precise pullout strength measurements of fasteners installed in a structure.

Another important feature of the present invention is that the portable fastener tester system facilitates obtaining highly repeatable results.

Another important feature of the present invention is that the portable fastener tester system is provided in an automated form which removes operator error and operator inconsistencies that add to inaccuracies in pullout strength measurement results.

Another important feature of the present invention is that the load cell is in the form of an S-block load cell which senses the amount of force applied to the fastener and transmits the sensed data to the control means.

Another important feature of the present invention is that the portable fastener tester system has a driving member that operates at a selectable constant rate of travel so to uniformly increase the amount of force acting on the fastener which facilitates the precise detection of when the force decreases and, hence, indicates the peak force.

Therefore, it can be readily appreciated that the present invention provides for highly accurate, precise, and repeatable pullout strength measurements of fasteners installed in a structure.

The foregoing has outlined rather broadly, the more pertinent and important features of the present invention.

The detailed description of the invention that follows is offered so that the present contribution to the art can be more fully appreciated. Additional features of the invention will be described hereinafter. These form the subject of the claims of the invention. It should be appreciated by those skilled in the art that the conception and the disclosed specific embodiment may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more succinct understanding of the nature and objects of the invention, reference should be directed to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
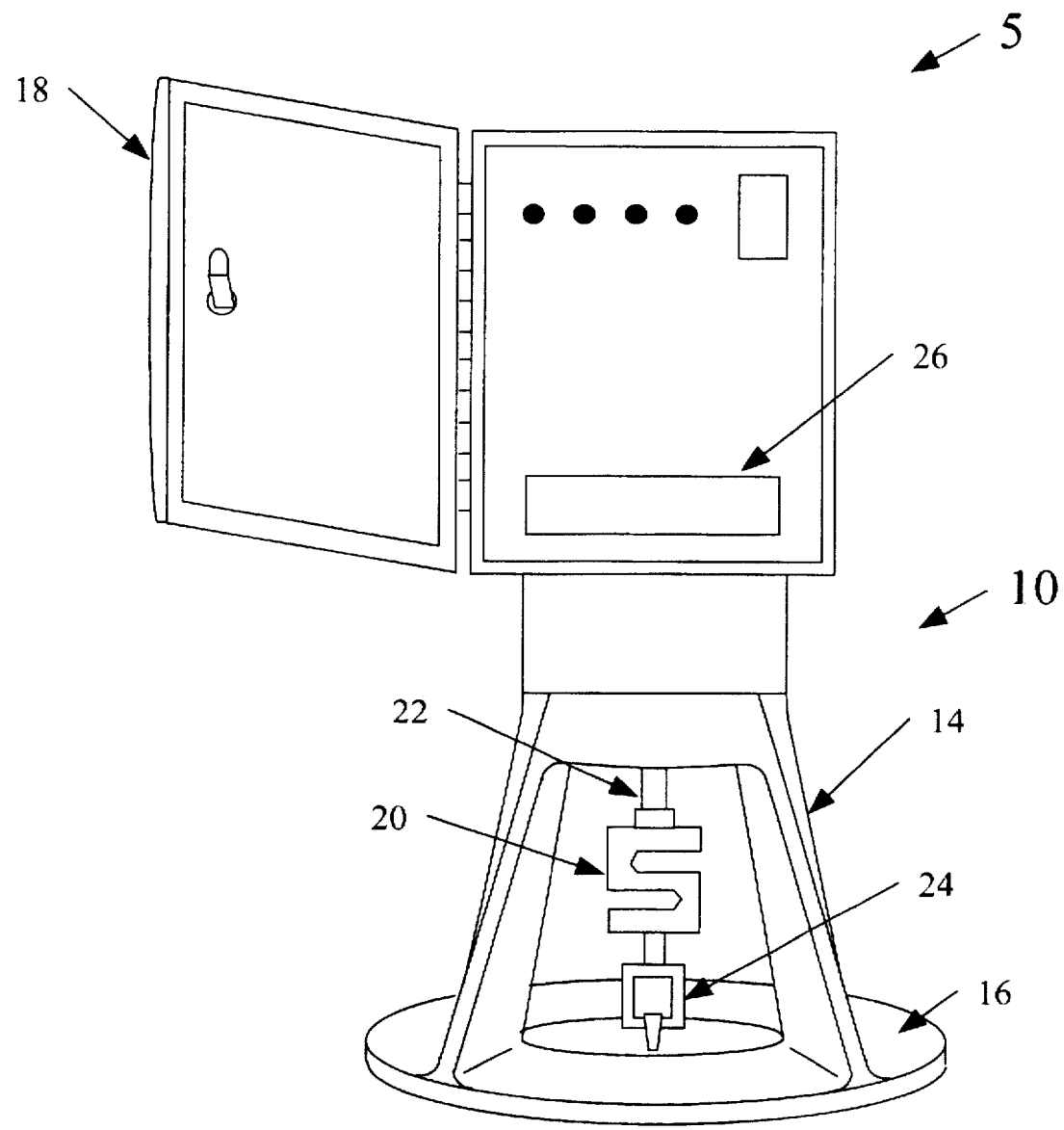
FIG. 1 is a frontal perspective view of the portable fastener tester system of the present invention illustrating the case housing, the support legs, the stabilizing foot, the load cell, and the lifter means in their relative positions to each other.

As shown in FIG. 1, the portable fastener tester system 5 of the present invention can be seen in a frontal view. The portable fastener tester system 5 can be seen to include a tester assembly, generally indicated by reference numeral 10, having a case housing 12, support legs 14, and a stabilizing foot 16. The case housing 12 can be seen to include a door 18 pivotally mounted on one side thereof to facilitate closing the case housing 12 when not in use and providing protection from inclement weather. The case housing is formed from a sturdy metallic material for protecting the critical components contained inside and withstanding impacts resulting from an accidental dropping. Further, a load cell 20, forming part of the control means, can be seen in its proper position coupled to a driving member 22 of the tester assembly 10. A lifter means 24 is coupled to the load cell 20. The lifter means 24 utilized in the preferred embodiment of the present invention is generally comprised of a U-shaped section having in-turned ends to facilitate the gripping of a fastener during tests. It is to be noted that various other configurations of the lifter means 24 exist in the industry today for accommodating the various other types of fasteners that are tested. It is important that the lifter means 24 be formed from a suitable material that is sufficiently strong to withstand the forces that are applied to a specific fastener during a test.

On the front of the portable fastener tester system 5 the display means 26 can be seen in the lower part of the case housing 12. The display means 26 is preferably in the form of a high contrast LED display device providing 2 lines of 16 characters. The display means 26 used in the preferred embodiment is a standard display readily available in the electronics industry. However, it is to be noted that other suitable displays may be utilized to accomplish the purpose of indicating the test results and communicating operational instructions to the user during tests.

Figure 2:
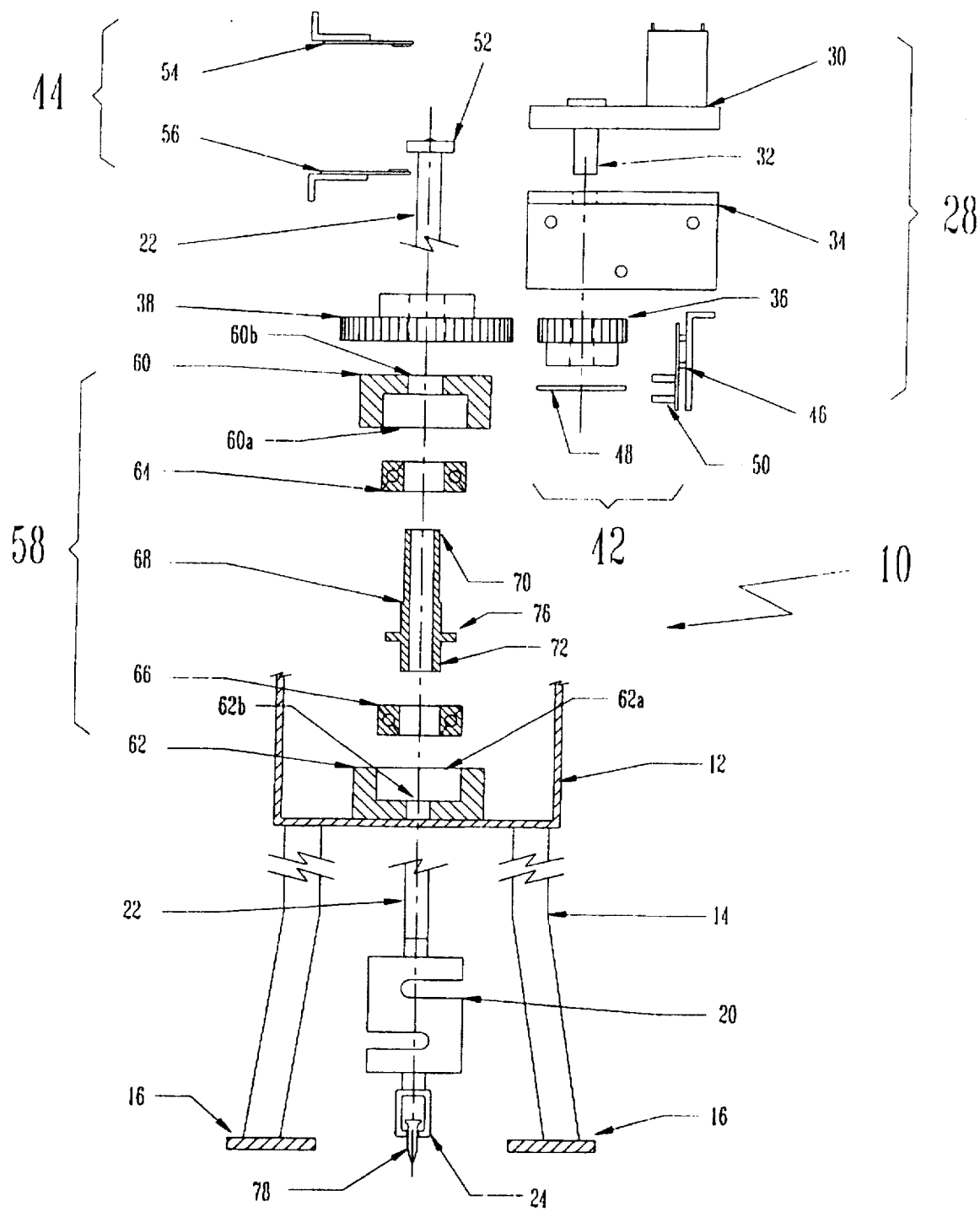
FIG. 2 is an exploded assembly view of tester assembly illustrating the various internal parts therein including the power nut assembly, the driving means, the load cell and the lifter means in their relative positions to each other.

In referring now to FIG. 2, tester assembly 10 can be seen in a detailed exploded assembly view illustrating the various components contained within the case housing 12. The driving means, generally indicated by reference numeral 28, can be seen to be comprised of a motor 30 having a shaft 32. The motor 30 and shaft 32 are coupled to a motor mount 34 which is, in turn, fixably coupled to the case housing 12 by way of standard bolts commonly used in the industry. The driving means 28 can be seen to include a small drive gear 36 coupled to the shaft 32 that cooperatively engages a large drive gear 38. The small and large drive gears 36 and 38 are preferably standard spur gears commonly available in the industry. The small and large drive gears 36 and 38, of the preferred embodiment, are specifically 28 and 56 teeth 14½ degrees P.A. type gears. The 28 teeth small drive gear 36 has a 1.750 in. pitch diameter and the large drive gear 38 has a 3.500 in. pitch diameter. The small and large drive gears 36 and 38 additionally have 1½ inch and 2 inch diameter hubs respectively. It is to be noted that other drive gears in varying combinations may be utilized to provide the necessary applied forces for carrying out the testing in other specific applications.

The motor 30 is preferably a DC motor capable of obtaining output RPM's from 0–800 and up to 100 in. lbs. of torque. The speed of the motor 30 is controlled and varied by way of pulse modulating the voltage supply provided to the motor 30 so as to vary the output RPM's and, hence, the resulting torque. The motor 30 of the present invention is specifically a twelve (12) volt DC motor having a 144.6 to 1 gear ratio and a continuous duty cycle. It is to be noted that other suitable types of motors may be utilized to provide the force requirements of the portable fastener tester system 5.

In FIG. 2, various components that further form part of the control means can also be seen. The control means is in part further comprised of a speed control means, generally indicated by reference numeral 42, and a limiter means, generally indicated by reference numeral 44. The speed control means 42 is comprised of an optical reader 46 and an opto chopper disc 48. The opto chopper disc 48 is coupled to the small drive gear 36 and extends outward to cooperate with the optical reader 46. The optical reader 46 is mounted to the motor mount 34 such that the opto chopper disc 48 rotates within sensors 50 of the optical reader 46. The limiter means 44 can be seen to be comprised of a limit magnet 52, an upper limit switch 54 and a lower limit switch 56. The limit magnet 52 is coupled to the extended end 22a of the driving member 22. The upper limit switch 54 is coupled to the case housing 12 and extends outward to cooperate with the limit magnet 52. The lower limit switch 56 is similarly coupled to the case housing 12 so as to extend outward and cooperate with the limit magnet 52.

In concentrating on the driving member 22 of the tester assembly 10, it can be seen that the driving member 22 extends down through a power nut assembly, generally indicated by reference numeral 58. The power nut assembly 58 can be seen to include: a first housing portion 60 having a partial large center bore 60a and a small center bore 60b; a second housing portion 62 having a partial large center bore 62a and a small center bore 62b; a first angular contact bearing 64 sized to be received within the partial large center bore 60a of the first housing portion 60; and a second angular contact bearing 66 sized to be received within the partial large center bore 62a of the second housing portion 62.

Contained within the power nut assembly 58 is a captured nut 68 having a first end 70, a second end 72, a center bore 74 and a flange 76. The first end 70 is received through the first angular contact bearing 64, the small center bore 60b of the first housing portion 60 and fixably coupled to the large drive gear 38. The first angular contact bearing 64 is to receive the captured nut 68 in such a manner so as to be positioned adjacent the flange 76. The second angular contact bearing 66 receives the second end 72 of the captured nut 68 in such a manner so as also to be positioned adjacent the flange 76 and thereby sandwiching the flange 76 therebetween. With the first and second angular contact bearings 64 and 66 positioned on the captured nut 68 and respectively received by the first and second housing portions 60 and 62, the captured nut 68 is resultantly rotatably retained within the power nut assembly 58. It is noted that the second housing portion 62 is rigidly fixed to the case housing 12 to facilitate the supporting of the power nut assembly 58, the captured nut 68 and the large drive gear 38 which is coupled to the driving member 22.

FIG. 2 additionally illustrates the support legs 14 and the stabilizing foot 16 extending from the case housing 12. The load cell 20 can be seen in its relative position coupled to the one end 22b of the driving member 22. The lifter means 24 is shown coupled to the load cell 20 and gripping a fastener 78.

The first and second angular contact bearings 64 and 66 are preferably standard contact bearings readily available in the industry suitable for handling the pullout strength forces required for the testing of various fasteners used in the roofing industry. It is to be noted herein that appropriate bearings may be selected on force handling capabilities as may be required by various different testing applications. The load cell 20 is preferably in the form of an S-block load cell that is readily available in the industry for sensing load characteristics. However, it is noted herein that various other forms of a load cell 20 may be utilized for accomplishing the load sensing function during testing, such as pancake, beam, ball and socket, miniature, and subminiature load cell forms that are readily available in the industry and may be more appropriate for a specific application.

Figure 3:
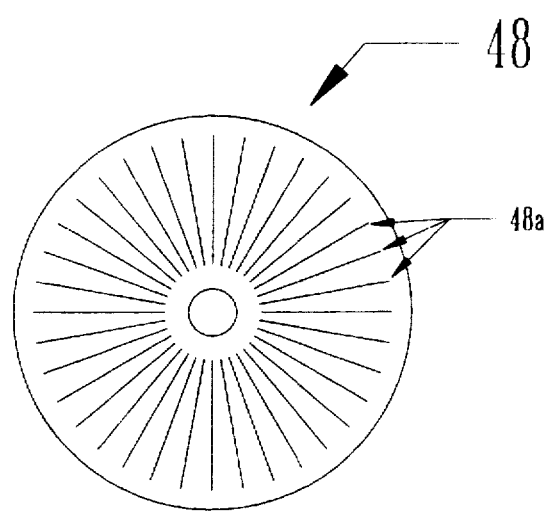
FIG. 3 is a top plan view of the opto chopper disc illustrating the precise configuration of lines radially aligned on the diameters.

In referring now specifically to FIG. 3, a top plan view of the opto chopper disc 48 can be seen. The opto chopper disc 48 can be seen to include a plurality of sense lines 48a extending radially from the center. The opto chopper disc 48 is formed from a transparent material thereby facilitating the readily sensing of the sense lines 48a by the sensors 50 of the optical reader 46.

Figures 4A, 4B:
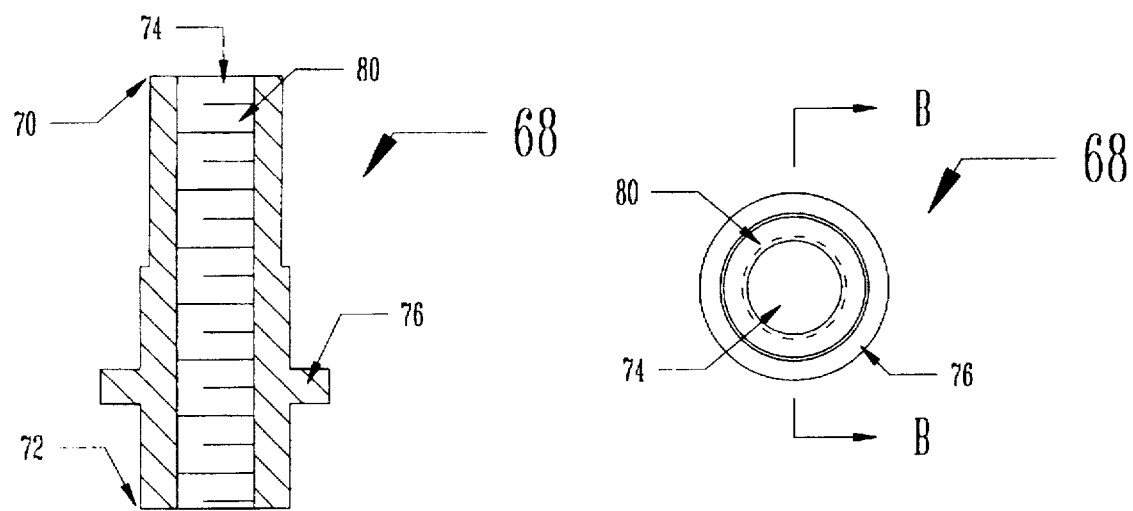
FIG. 4a is a top view of the captured nut illustrating the first end, the center bore, the flange extending radially outward and the internal threads in their relative positions to each other.
FIG. 4b is a cross sectional view of the captured nut taken along the line B—B in FIG. 4a, illustrating the flange extending radially outward, the first end, the second end and the internal threads in their relative positions to each other; the power nut assembly illustrating the small center bore, the satellite holes spaced thereabout, the partial large center bore, the key notch, and the set screw hole in their relative positions to each other.

In referring now to FIG. 4a, a top plan view of the captured nut 68 can be seen. The flange 76 extends radially outward from the captured nut 68. Additionally, internal threads 80 can be seen within the center bore 74.

In referring now to FIG. 4b, a cross-sectional elevational view of the captured nut 68 can be seen as taken along the line B—B in FIG. 4a. The first end 70, the second end 72, the center bore 74, and the internal threads 80 can be seen in more detail in their relative positions to each other. The flange 76 can be seen to be located nearer the second end 72 to facilitate limiting the amount of the second end 72 that is received within the second angular contact bearing 66 and second housing portion 62. The second end 72 is resultantly prevented from contacting the second housing portion 62 by way of the flange 76 contacting the second angular bearing.

Figure 5A:
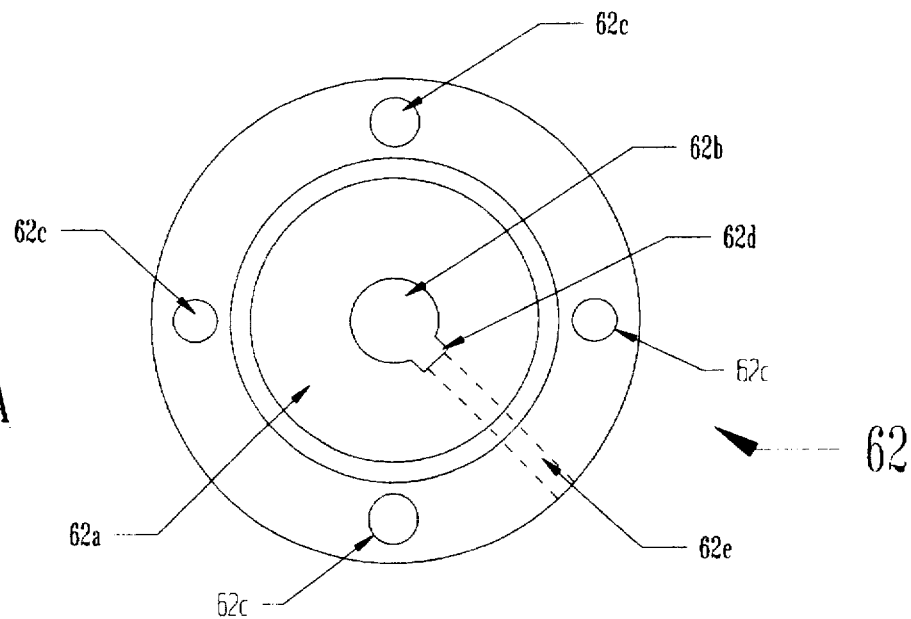
FIGS. 5a and 5b are top and side elevational views of the second housing portion of the power nut assembly illustrating the satellite holes, the small center bore, the partial large center bore, the key notch and the set screw hole in their relative positions to each other.

In referring now specifically to FIG. 5a, a top plan view of the second housing portion 62 is illustrated. The second housing portion 62 can be seen to further comprise satellite holes 62c positioned radially thereabout, a key notch 62d in the small center bore 62b and a set screw hole 62e. The set screw hole 62e facilitates the receiving of a set screw 82 (see FIG. 6) therethrough to partially invade the key notch 62d.

Figure 5B:
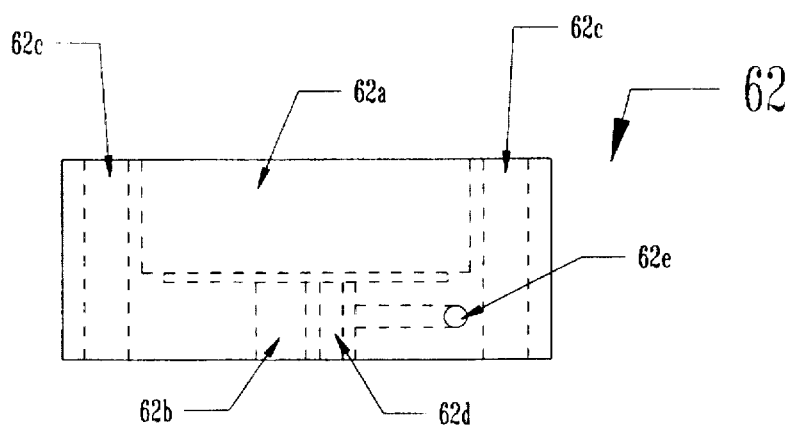

In referring now to FIG. 5b, a side elevational view of the second housing portion 62 can be seen illustrating the relative positions of the satellite holes 62c, the small center bore 62b, the key notch 62d, the set screw hole 62e and the partial large center bore 62a.

Figure 6:
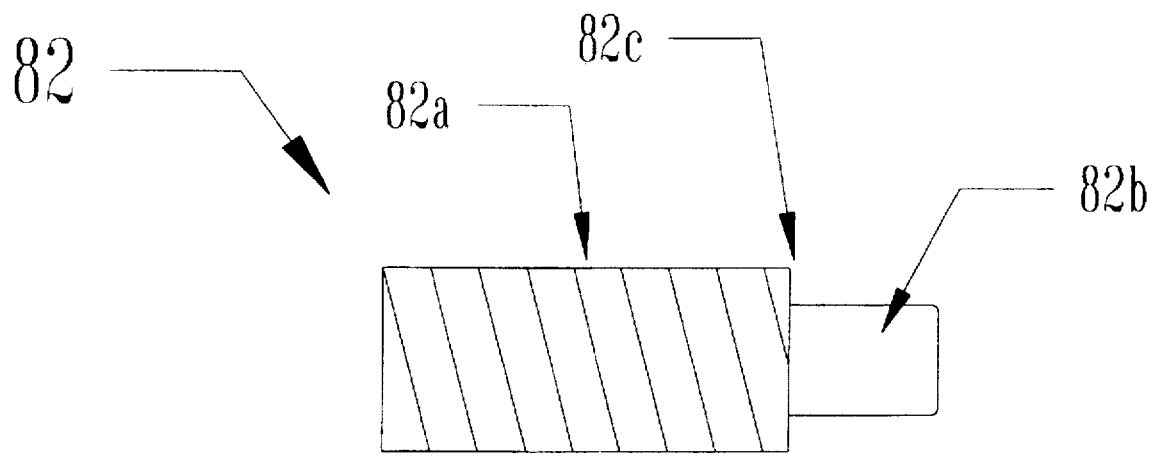
FIG. 6 is a top plan view of the set screw illustrating the main body and the extended portion in their relative positions to each other.

In referring now to FIG. 6, a side view of the set screw 82 can be seen. The set screw 82 includes a main body 82a, and an extended portion 82b positioned at one end 82c. The main body 82a is threadingly received by the set screw hole 62e whereby the extended portion 82b extends out of the set screw hole 62e into the key notch 62d.

Figure 7:
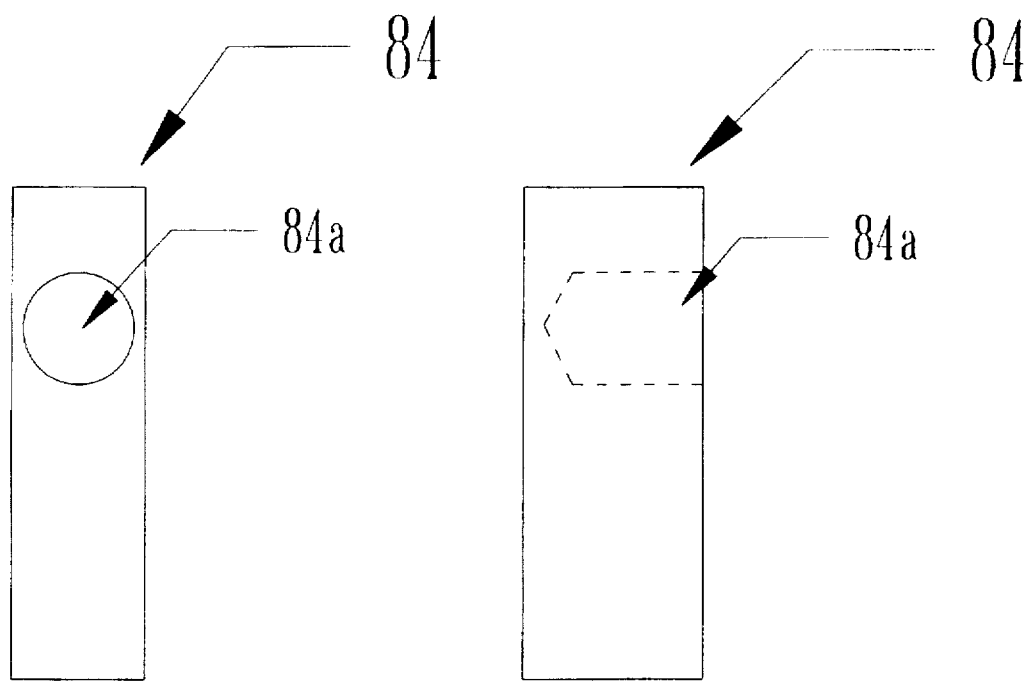
FIGS. 7a and 7b are respective front and side elevational views of the key block illustrating the position of the partial ream therein.

In referring now to FIGS. 7a and 7b, a key block 84 can be seen. The key block 84 is received by the key notch 62d of the second housing portion 62. The key block 84 further includes a ream 84a positioned so as to cooperatively receive the extended portion 82b of the set screw 82 when the key block 84 is installed in the key notch 62d of the second housing portion 62.

Figure 8:
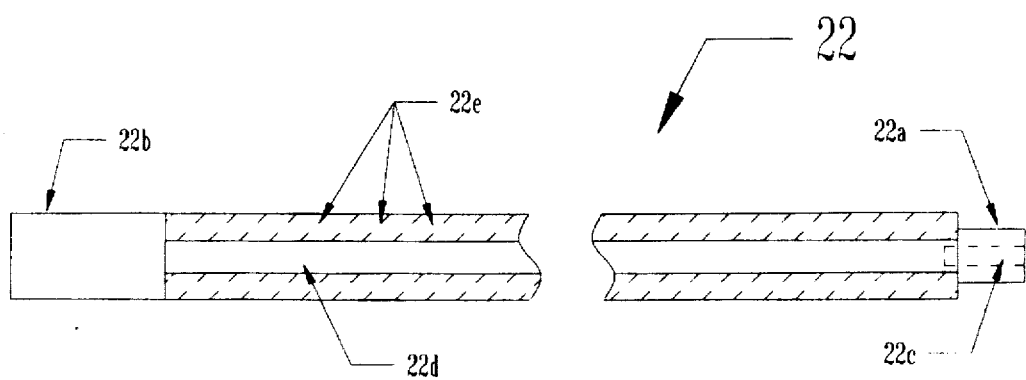
FIG. 8 is a side view of the driving member illustrating the extended end, the one end, the slot running longitudinally therealong and the partial center ream in their relative positions to each other.

In referring now specifically to FIG. 8, a side view of the driving member 22 can be seen. The driving member 22 includes an extended end 22a, one end 22b, a center partial ream 22c and a slot 22d running the length of the driving member 22. The extended end 22a facilitates receiving the limit magnet 52 by way of the center partial ream 22c threadingly receiving a retaining screw (not shown). The driving member 22 further includes external threads 22e to facilitate threaded translatable engagement with the captured nut 68. The slot 22d facilitates slidingly receiving the key block 84 therein so to prevent the driving member 22 from rotating during the rotation of the captured nut 68 about the driving member 22. With the driving member 22 being prevented from rotating, the rotational action of the captured nut 68 causes the driving member 22 to threadingly translate vertically relative to the captured nut 68. The one end 22b facilitates having the load cell 20 rigidly fixed thereto. It is noted that the driving member 22 and all of the force bearing components are to be formed from a sufficiently high strength material to facilitate the handling of the load forces required for performing the pullout strength test on a fastener 78.

Figure 9:
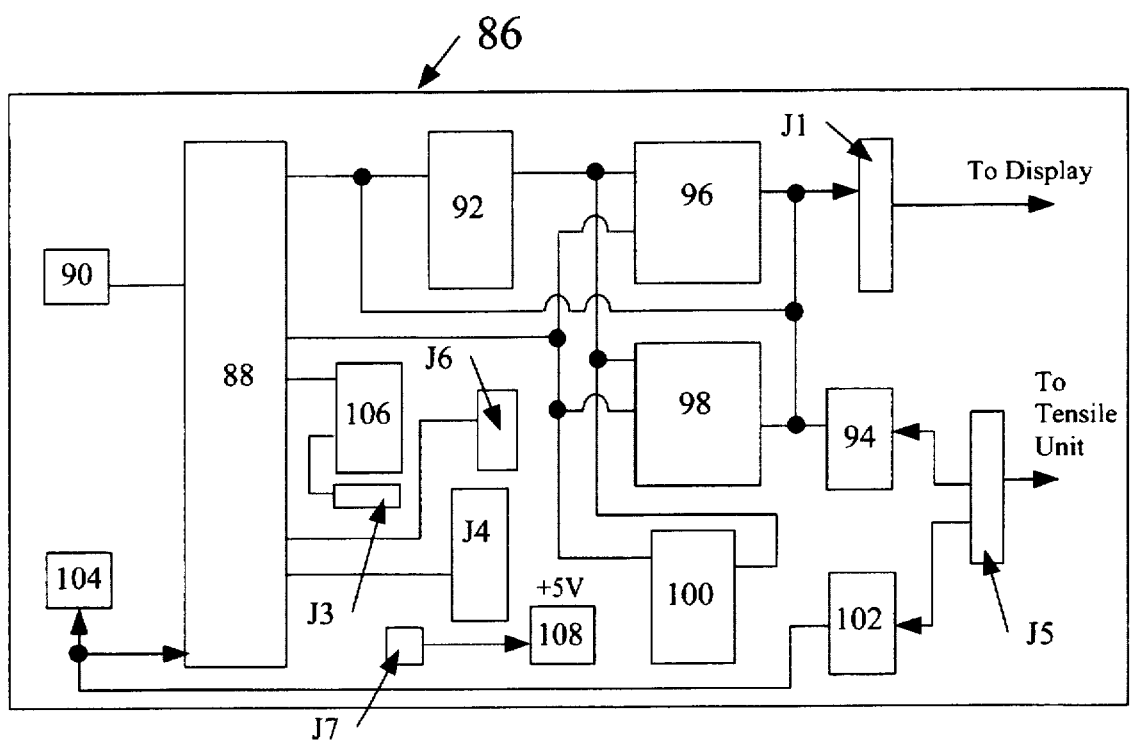
FIG. 9 is a schematic in block diagram form illustrating the electrical coupling of the various components within the electronic processing unit as is utilized in the present invention.

In now referring to FIG. 9, the electronic processing unit 86, which also forms part of the control means, can be seen in block diagram form. The electronic processing unit 86 is run by a microprocessor 88. The microprocessor 88 facilitates the performing of various calculation functions, the manipulation of data, and the determination of control related decisions. The microprocessor 88 is synchronized by a crystal 90 electrically coupled thereto that provides an eight (8) MHz clock cycle. The microprocessor 88 utilizes line drivers 92 and 94 for receiving data and transmitting instructions to other components. The microprocessor 88 utilizes line driver 92 for accessing address lines on the static RAM 96, address lines on the EPROM 98 and address lines on the programmable logic chip 100. Line driver 94 is utilized by the microprocessor 88 for communicating with the load cell 20.

The microprocessor 88 further communicates with the address lines and data lines of the EPROM 98 for receiving stored instructions that are programmed into the eprom 98 by way of a burning in process. The static RAM 96 facilitates the data storage functions within the electronic processing unit 86 in the form of facilitating the reading of data therefrom and the writing of data thereto. The EPROM 98 facilitates the storage of instructional code previously programmed therein for being accessed and read by the microprocessor 88 during the operation of the portable fastener tester system 5. The line drivers 92 and 94 function similar to octal D-type transparent latches for the purpose of propagating data to and from the microprocessor 88. The programmable logic chip 100 functions as an address decoder thereby dictating where data is to be sent to for storage and from where data is to be reaccessed by the microprocessor 88.

In receiving the analog data transmitted from the load cell 20, the data is first converted to 16-bit data words by an A/D converter 102 which then subsequently transmits the 16-bit digital data to the microprocessor 88. Further, a reset chip 104 communicates with the A/D converter 102 and the microprocessor 88 for the purposes of holding the microprocessor 88 in reset mode until the power to the microprocessor 88 is stable. Finally, a RS 232 driver/receiver chip 106 is electrically coupled to the microprocessor 88 for facilitating the converting of serial TTL signals to RS 232 levels thereby providing for the communication with external computers.

It is further noted that the static ram 96 facilitates the storage of the recorded force data and the associated test control settings that the test was performed in accordance with. Additionally, the recorded force data and associated test control settings may be stored in such a manner that the user may assign one of a plurality of location designators within at least one of a plurality of site designators to the data. This facilitates maintaining the integrity of the test results when tests are conducted at various sites and at a plurality of locations within each site. Furthermore, the tests results can then be downloaded from the portable fastener tester system 5 directly to an external computer thereby further maintaining the integrity of the test results.

Additionally, FIG. 9 illustrates the relative positions of the various connectors utilized by the electronic processing unit 86 which provide the necessary electrical connections with the various control components in the portable fastener tester system 5. Connector J1 is the display interface facilitating the electrical connection of the display means 26. Connector J3 is a serial interface facilitating the electrical connection of the electronic processing unit 86 to an outside computer. Connector J4 is the interface providing for the electrical connection of the limiter means 44 to the microprocessor 88. Connector J5 provides for the electrical connection of the load cell 20 to the microprocessor 88 by way of line driver 94 and the A/D converter 102. Connector J6 is the interface providing for the electrical connection of the optical reader 46 to the microprocessor 88. Connector J7 is the battery interface providing for the electrical connection of a battery (not shown) to the electronic processing unit 86. It is to be noted that the battery interface J7 electrically couples the voltage from a battery to a voltage regulator 108 before biasing up the electronic processing unit 86. A standard 12 volt DC battery is utilized in the embodiment of the portable fastener tester system 5 of the present invention. The voltage regulator 108 facilitates receiving the input voltage from the battery and outputting a constant +5 volts to bias up the electronic processing unit 86.

In the designing and building of the preferred embodiment of the electronic processing unit 86, standard electronic components commonly available in the industry were utilized for performing the respective electrical functions as described above within the electronic processing unit 86. It is to be understood that an electronic processing unit 86 may be formed from individual electronic components that differ from that as described in the preferred embodiment above, however, it is the intended function of the electronic processing unit 86 to perform the processing functions necessary to control the portable fastener tester system 5, calculate the resulting pullout strength measurements, record the force data and display the results to the user.

Now that the structure of the portable fastener tester system 5 has been described in detail, its operation may readily be understood. In testing a fastener 78, the portable fastener tester system 5 is positioned over the fastener 78 with the lifter means 24 in operable engagement with the fastener 78. The electronic processing unit 86 is interfaced with and set to perform calibration functions and ultimately initiate a test. The setup and calibration of the portable fastener tester system 5 is performed in accordance with instruction provided by the electronic processing unit 86 which has been stored in the eprom 98. Once the calibration and set up is complete, the fastener 78 is engaged by the lifter means 24 and a test is initiated.

After initiation, the motor 30 is supplied a voltage bias thereby causing the shaft 32 to rotate with the small drive gear 36 engaging the large drive gear 38 which, in turn, forceably rotates the captured nut 68, retained within the power nut assembly 58, about the driving member 22. While the small drive gear 36 is rotating in accordance with the shaft 32, the opto chopper disc 48 is simultaneously rotating at the same RPM's as the shaft 32 and being sensed by the sensors 50 of the optical reader 46. The sensors 50 are sensing the sense lines 48a on the opto chopper disc 48 and transmitting electrical data to the electronic processing unit 86 wherein the microprocessor 88 acts upon the received data so to constantly monitor and control the speed of the motor 30. Thus, the microprocessor 88 can ultimately precisely control and ensure a constant rate of travel of the driving member 22 and fastener 78 by controlling the speed of the motor 30. The speed of the motor 30 is, in effect, controlled by way of the microprocessor 88 varying the bias voltage being supplied to the motor 30 which can produce a reduction or increase in the speed of the motor 30.

As the captured nut 68 is rotating within the power nut assembly 58, the driving member 22 is forceably being translated vertically upwards so to apply a pulling force on the fastener 78. When being translated vertically upward the driving member 22 is prevented from rotating as the captured nut 68 rotates by way of the key block 84 positioned in the key notch 62d of the second housing portion 62. The key block 84 is sized to slide along the slot 22d of the driving member 22 during periods of vertical displacement. The load cell 20 transmits to the electronic processing unit 86 the amount of pulling force delivered by the driving member 22 to the fastener 78 as the driving member 22 is raised. The display means 26 will display the continuous and peak forces sensed by the load cell 20. The test continues until one of three situations occur. First, the test will stop when the operator stops pressing the up switch to shut off the motor 30. Second, the test will stop if the maximum capacity of the load cell 20 is reached wherein the microprocessor 88 will automatically shut off the motor 30. Or third, the test will stop if the driving member 22 is continually raised until the limit magnet 52 contacts the upper limit switch 54 so as to automatically turn off the motor 30.

After the test is finished, the driving member 22 is translated down to a beginning position wherein the lifter means 24 may be engaged with another fastener 78 to begin another test. Once again, the motor 30 will be stopped if the limit magnet 52 contacts the lower limit switch 56 when the driving member 22 is being translated downward.

The present disclosure includes that contained in the appended claims, as well as that of the foregoing description. Although this invention has been described in its preferred form with a certain degree of particularity, it should be understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A portable fastener tester system for testing the pullout strength of a fastener secured to a structure, said portable fastener tester system comprising in combination:
 a tester assembly capable of being positioned on the structure to facilitate testing of the fastener, said tester assembly including a driving member capable of being coupled relative to the fastener;
 control means for controlling the operation of said tester assembly so as to act upon said driving member and apply force upon the fastener to translate the fastener at a constant rate thereby resulting in translation of the fastener at a constant rate and indicating measurement results, said control means being coupled to said tester assembly; and
 driving means for applying force upon said driving member, said driving means being coupled relative to said driving member of said tester assembly,
 whereby said tester assembly is positioned on the structure in coupled relation to the fastener to be tested and said control means initiates operation of said tester assembly and controls said driving means thereby facilitating precise pullout strength determination of the fastener and indicating such.

2. The portable fastener tester system as recited in claim 1, wherein said driving means is comprised of a motor coupled to said tester assembly and electrically coupled relative to said control means, said motor being controlled by said control means so to facilitate the conducting of pullout strength measurements.

3. The portable fastener tester system as recited in claim 2, wherein said driving means further comprises a shaft coupled to said motor, a small drive gear coupled to said shaft, and a large drive gear coupled relative to said driving member and positioned so to cooperate with and engage said small drive gear, whereby said large drive gear serves to transfer force to said driving member so to act upon the fastener being tested.

4. The portable fastener tester system as recited in claim 3, wherein said driving means further comprises a motor mount coupled to said tester assembly, said motor mount facilitating the securing of said motor to said tester assembly in operable position relative to said large drive gear.

5. The portable fastener tester system as recited in claim 4, wherein said small and said large drive gears are in the form of spur gears designed for engaged operation with each other.

6. The portable fastener tester system as recited in claim 1, wherein said control means is comprised of an electronic processing unit and a load cell electrically coupled thereto, said load cell being coupled relative to the fastener and said driving member thereby producing electrical signals proportionate to the force being exerted on the fastener so to facilitate determining pullout strength.

7. The portable fastener tester system as recited in claim 6, wherein said control means is further comprised of speed control means for controlling the speed of the driving means, and limiter means for establishing the range of force that may be exerted on the fastener by said driving means, said speed control means being electrically coupled to said driving means and said electronic processing unit, said limiter means being coupled relative to said driving member and electrically coupled to said electronic processing unit.

8. The portable fastener tester system as recited in claim 7, wherein said speed control means is comprised of an opto chopper disc and an optical reader, said opto chopper disc being coupled to said driving means and said optical reader being operatively positioned relative to said opto chopper disc, said optical reader facilitating sensing the rotation of said opto chopper disc.

9. The portable fastener tester system as recited in claim 7, wherein said limiter means is comprised of a limit magnet coupled to the driving member, a maximum limit switch and a minimum limit switch, said maximum and minimum limit switches being coupled to said tester assembly and operatively positioned relative to said limit magnet so to cooperate therewith and establish maximum and minimum travel distances of the driving member.

10. The portable fastener tester system as recited in claim 6, wherein said load cell is in the form of an s-block load cell electrically coupled to said electronic processing unit, said load cell being coupled relative to the fastener and facilitating determining pullout strength of the fastener.

11. The portable fastener tester system as recited in claim 6, wherein said control means is further comprised of display means for displaying the continuous and peak load forces during testing.

12. The portable fastener tester system as recited in claim 1, wherein said tester assembly further comprises a case housing, a power nut assembly coupled to said case housing, and a captured nut having a first end and a second end, said captured nut being rotatably retained within said power nut assembly, said captured nut further being sized to receive said driving member.

13. The fastener tester system as recited in claim 12, wherein said power nut assembly further includes a first housing portion and a second housing portion, said second housing portion being coupled to said case housing and said first and second ends of said captured nut being respectively received by said first and second housing portions so to facilitate retaining said captured nut therebetween.

14. The portable fastener tester system as recited in claim 13, wherein said power nut assembly further includes a first and a second angular contact bearing, said first and second angular contact bearings being respectively coupled to said first and second ends of said captured nut, said first and second angular contact bearings being sized to be respectively received by said first and second housing portions of said power nut assembly.

15. The portable fastener tester system as recited in claim 12, wherein said captured nut further includes a flange positioned between said first and second ends and extending radially outward, said flange engaging said second angular contact bearing and facilitating preventing said second end of said captured nut from contacting said second portion of said power nut assembly.

16. The portable fastener tester system as recited in claim 1, wherein said tester assembly further includes lifter means for releasably engaging the fastener, said lifter means being coupled relative to said driving member.

17. A method for determining the pullout strength of fasteners comprising the steps of:

providing a portable fastener tester system comprised of a tester assembly having a driving member, control means for controlling the operation of the tester assembly and indicating measurement results, and driving means for applying force upon the driving member;

providing a load cell for producing an electrical signal of a level that is proportional to applied force;

engaging the fastener with the load cell and driving member;

applying force to the driving member so to impart a pulling force on the fastener to cause the fastener to translate at a constant rate of travel so to facilitate determining the precise minimum amount of force required to dislodge the fastener and achieve a high measurement resolution;

continuously monitoring and recording the force being applied to the fastener over the length of the test;

tracking the changes in force to determine the peak amount of force imparted on the fastener that initialized a dislodging of the fastener and pulled out the fastener; and displaying the peak force for the completed test.

18. The method as recited in claim 17 further comprising the steps of:

stopping the applied force when a certain vertical displacement of the driving member has occurred;

displacing the driving member downward until the fastener is released.

19. The method as recited in claim 17, wherein the step of monitoring and recording the force being applied to the fastener further comprises the steps of: storing the test control settings in the control means; obtaining a plurality of force readings for the continuous duration of the test; tracking and storing the highest force reading in the control means; comparing the continuous force reading with the current highest force reading; and displaying the continuous and highest force readings for the complete test.

20. The method as recited in claim 17, wherein the step of continuously monitoring and recording the force being applied to the fastener over the length of the test is further comprised of the steps of: assigning one of a plurality of location designators within at least one of a plurality of site designators to the recorded force data and associated test control settings; and storing the force data and associated test control settings within the control means in accordance with such designations.

21. The method as recited in claim 20 further comprising the steps of: electrically coupling the portable fastener testing system to a computer; and downloading the recorded force data and associated test control settings from the control means to the computer in accordance with the site and location designations initially assigned so to thereby maintain test result integrity.

* * * * *